(12) United States Patent
Kennedy et al.

(10) Patent No.: US 8,847,799 B1
(45) Date of Patent: Sep. 30, 2014

(54) METHODS AND SYSTEMS FOR STORING SEQUENCE READ DATA

(71) Applicant: Good Start Genetics, Inc., Cambridge, MA (US)

(72) Inventors: Caleb J. Kennedy, Arlington, MA (US); Niru Chennagiri, Lexington, MA (US)

(73) Assignee: Good Start Genetics, Inc., Cambridge, MA (US)

( * ) Notice: Subject to any disclaimer, the term of this patent is extended or adjusted under 35 U.S.C. 154(b) by 0 days.

(21) Appl. No.: 14/293,568

(22) Filed: Jun. 2, 2014

Related U.S. Application Data

(60) Provisional application No. 61/830,540, filed on Jun. 3, 2013.

(51) Int. Cl.
| | |
|---|---|
| *H03M 7/30* | (2006.01) |
| *G06F 19/00* | (2011.01) |
| *G06F 19/18* | (2011.01) |
| *C12Q 1/44* | (2006.01) |
| *C12Q 1/68* | (2006.01) |
| *C12N 15/10* | (2006.01) |
| *G06F 19/22* | (2011.01) |

(52) U.S. Cl.
CPC .............. *H03M 7/3059* (2013.01); *G06F 19/18* (2013.01); *C12Q 1/44* (2013.01); *C12Q 1/6827* (2013.01); *H03M 7/30* (2013.01); *G06F 19/32* (2013.01); *C12N 15/10* (2013.01); *H03M 7/70* (2013.01); *G06F 19/22* (2013.01)
USPC ............................................. 341/87; 702/20

(58) Field of Classification Search
CPC .......... H03M 7/30; G06F 19/22; G06F 19/18; C12N 15/10; C12Q 1/6827; C12Q 1/6883; C12Q 1/44
USPC ......... 341/87; 702/19, 20; 435/91.52, 6.12, 6, 435/6.1
See application file for complete search history.

(56) References Cited

U.S. PATENT DOCUMENTS

| | | | |
|---|---|---|---|
| 4,683,195 | A | 7/1987 | Mullis et al. |
| 4,683,202 | A | 7/1987 | Mullis |
| 4,988,617 | A | 1/1991 | Landegren et al. |
| 5,234,809 | A | 8/1993 | Boom et al. |
| 5,242,794 | A | 9/1993 | Whiteley et al. |
| 5,494,810 | A | 2/1996 | Barany et al. |
| 5,583,024 | A | 12/1996 | McElroy |
| 5,604,097 | A | 2/1997 | Brenner |
| 5,674,713 | A | 10/1997 | McElroy |
| 5,695,934 | A | 12/1997 | Brenner |
| 5,700,673 | A | 12/1997 | McElroy |

(Continued)

OTHER PUBLICATIONS

Balzer, 2013, Filtering duplicate reads from 454 pyrosequencing data, Bioinformatics 29(7):830-836.

(Continued)

*Primary Examiner* — Joseph Lauture
(74) *Attorney, Agent, or Firm* — Thomas C. Meyers; Brown Rudnick LLP

(57) ABSTRACT

The present invention generally relates to storing sequence read data. The invention can involve obtaining a plurality of sequence reads from a sample, identifying one or more sets of duplicative sequence reads within the plurality of sequence reads, and storing only one of the sequence reads from each set of duplicative sequence reads in a text file using nucleotide characters.

15 Claims, 7 Drawing Sheets

(56) References Cited

U.S. PATENT DOCUMENTS

| | | | |
|---|---|---|---|
| 5,846,719 | A | 12/1998 | Brenner et al. |
| 5,863,722 | A | 1/1999 | Brenner |
| 6,138,077 | A | 10/2000 | Brenner |
| 6,150,516 | A | 11/2000 | Brenner et al. |
| 6,172,214 | B1 | 1/2001 | Brenner |
| 6,172,218 | B1 | 1/2001 | Brenner |
| 6,210,891 | B1 | 4/2001 | Nyren et al. |
| 6,235,475 | B1 | 5/2001 | Brenner et al. |
| 6,306,597 | B1 | 10/2001 | Macevicz |
| 6,352,828 | B1 | 3/2002 | Brenner |
| 6,582,938 | B1 | 6/2003 | Su et al. |
| 6,828,100 | B1 | 12/2004 | Ronaghi |
| 6,833,246 | B2 | 12/2004 | Balasubramanian |
| 6,911,345 | B2 | 6/2005 | Quake et al. |
| 7,232,656 | B2 | 6/2007 | Balasubramanian et al. |
| 7,393,665 | B2 | 7/2008 | Brenner |
| 7,537,897 | B2 | 5/2009 | Brenner et al. |
| 7,544,473 | B2 | 6/2009 | Brenner |
| 7,598,035 | B2 | 10/2009 | Macevicz |
| 7,776,616 | B2 | 8/2010 | Heath et al. |
| 7,835,871 | B2 | 11/2010 | Kain et al. |
| 7,957,913 | B2 | 6/2011 | Chinitz et al. |
| 7,960,120 | B2 | 6/2011 | Rigatti et al. |
| 8,209,130 | B1 | 6/2012 | Kennedy et al. |
| 2002/0190663 | A1 | 12/2002 | Rasmussen |
| 2006/0024681 | A1 | 2/2006 | Smith et al. |
| 2006/0292611 | A1 | 12/2006 | Berka et al. |
| 2007/0114362 | A1 | 5/2007 | Feng et al. |
| 2008/0081330 | A1 | 4/2008 | Kahvejian |
| 2009/0026082 | A1 | 1/2009 | Rothberg et al. |
| 2010/0285578 | A1 | 11/2010 | Selden et al. |
| 2010/0300559 | A1 | 12/2010 | Schultz et al. |
| 2010/0300895 | A1 | 12/2010 | Nobile et al. |
| 2010/0301398 | A1 | 12/2010 | Rothberg et al. |
| 2010/0304982 | A1 | 12/2010 | Hinz et al. |
| 2011/0009278 | A1 | 1/2011 | Kain et al. |
| 2011/0301042 | A1 | 12/2011 | Steinmann et al. |
| 2012/0115736 | A1* | 5/2012 | Bjornson et al. ............ 506/2 |

OTHER PUBLICATIONS

Bonfield, 2013, Compression of FASTQ and SAM format sequencing data, PLoS One 8(3):e59190.
Bose, 2012, BIND—An algorithm for loss-less compression of nucleotide sequence data, J Biosci 37(4):785-789.
Chevreux, 1999, Genome Sequence Assembly Using Trace Signals and Additional Sequence Information, Computer Science and Biology: Proceedings of the German Conference on Bioinformatics (GCB) 99:45-56.
Cock, 2009, The Sanger FASTQ file format for sequences with quality scores, and the Solexa/Illumina FASTQ variants, Nucleic Acids Res 38(6):1767-1771.
Danecek et al., 2011, The variant call format and VCFtools, Bioinformatics 27(15):2156-2158.
delaBastide, 2007, Assembling genomic DNA sequences with PHRAP, Curr Protoc in Bioinformatics, 17(11.4)1-15.
Deorowicz, 2013, Data compression for sequencing data, Alg for Mole Bio 8:25.
DiGuistini et al., 2009, De novo sequence assembly of a filamentous fungus using Sanger, 454 and Illumina sequence data, Genome Biology, 10:R94.
Dudley, 2009, A quick guide for developing effective bioinformatics programming skills, PLoS Comp Biol 5(12): e1000589.
Faust, 2014, SAMBLASTER: fast duplicate marking and structural variant read extraction, Bioinformatics published online May 7, 2014.
Guerrero-Fernandez, 2013, FQbin: a compatible and optimize dformat for storing and managing sequence data, IWBBIO Proceedings, Granada 337-344.

Homer, 2009, BFAST: An alignment tool for large scale genome resequencing, PLoS One 4(11):e7767.
Iqbal, 2012, De novo assembly and genotyping of variants using colored de Bruijn graphs, Nature Genetics 44:226-232.
Kumar, 2010, Comparing de novo assemblers for 454 transcriptome data, Genomics 11:571.
Langmead et al., 2009, Ultrafast and memory-efficient alignment of short DNA sequences to the human genome, Genome Biology 10:R25.
Larkin, 2007, Clustal W and Clustal X version 2.0, Bioinformatics, 23(21):2947-2948.
Li & Durbin, 2009, Fast and accurate short read alignment with Burrows-Wheeler Transform, Bioinformatics 25:1754.
Li, 2009, The Sequence Alignment/Map format and SAMtools, Bioinformatics 25(16):2078-9.
Li, 2011, Improving SNP discovery by base alignment quality, Bioinformatics 27:1157.
Li, 2014, HUGO: Hierarchical mUlti-reference Genome cOmpression for aligned reads, JAMIA 21:363-373.
Lin, 2008, Zoom! Zillions of Oligos Mapped, Bioinformatics 24:2431.
Margulies, 2005, Genome sequencing in micro-fabricated high-density picotiter reactors, Nature, 437:376-380.
Miller, 2010, Assembly algorithms for next-generation sequencing data, Genomics 95:315-327.
Mills et al., 2010, Mapping copy number variation by population-scale genome sequencing, Nature 470:59-65.
Mohammed, 2012, DELIMINATE—a fast and efficient methods for loss-less compression of genomice sequences, Bioinformatics 28(19):2527-2529.
Moudrianakis & Beer, 1965, Base sequence determination in nucleic acids with the electron microscope, III. Chemistry and microscopy of guanine-labeled DNA, PNAS 53:564-71.
Ning et al., 2001, SSAHA: A fast search method for large DNA databases, Genome Research 11(10):1725-9.
Pearson & Lipman, 1988, Improved tools for biological sequence comparison, PNAS 85:2444-2448.
Pertea et al., 2003, TIGR Gene indices clustering tools (TGICL): a software system for fast clustering of large EST datasets, Bioinformatics 19(5):651-52.
Pinho, 2013, MFCompress: a compression tool for FASTA and multi-FASTA data, Bioinformatics 30(1):117-8.
Rothberg, 2011, An integrated semiconductor device enabling non-optical genome sequencing, Nature 475:348-352.
Sievers, 2011, Fast, scalable generation of high-quality protein multiple sequence alignments using Clustal Omega, Mol Syst Biol 7:539.
Simpson, 2009, ABySS: A parallel assembler for short read sequence data, Genome Res., 19(6):1117-23.
Soni, 2007, Progress toward ultrafast DNA sequence using solid-state nanopores, Clin Chem 53(11):1996-2001.
Spanu, 2010, Genome expansion and gene loss in powdery mildew fungi reveal tradeoffs in extreme parasitism, Science 330(6010):1543-46.
Veeneman, 2012, Oculus: faster sequence alignment by streaming read compression, BMC Bioinformatics 13:297.
Warren, 2007, Assembling millions of short DNA sequences using SSAKE, Bioinformatics, 23:500-501.
Xu, 2012, FastUniq: A fast de novo duplicates removal tool for paired short reads, PLoS One 7(12):e52249.
Zerbino, 2008, Velvet: Algorithms for de novo short read assembly using de Bruijn graphs, Genome Research 18 (5):821-829.
Zhao, 2009, PGA4genomics for comparative genome assembly based on genetic algorithm optimization, Genomics. 94(4):284-6.
Zheng, 2011, iAssembler: a package for de novo assembly of Roche-454/Sanger transcriptome sequences, BMC Bioinformatics 12:453.
Zhou, 2014, Bias from removing read duplication in ultra-deep sequencing experiments, Bioinformatics 30 (8):1073-1080.

* cited by examiner

Sample1.fa

>Read1
ACGATCC

>Read 2
ACGATCC

>Read3
ACGGTTA

>Read4
ACGGTTA

>Read5
ACGGTTA

>Read6
CGACATA

>Read7
ACAGACC

>Read8
ACAGACC

...

Sample2.fa

>Read1
ACGGTTA

>Read2
ACGGTTA

>Read3
CGACATA

>Read4
ACAGACC

>Read5
ACAGATT

>Read6
ACAGATT

MasterReadsFile.txt

ACGATCC
ACGGTTA
CGACATA
ACAGACC
ACAGATT
...

FIG. 3

METHODS AND SYSTEMS FOR STORING SEQUENCE READ DATA

CROSS-REFERENCE TO RELATED APPLICATION

This application claims the benefit of, and priority to, U.S. Provisional Patent Application No. 61/830,540, filed Jun. 3, 2013, the contents of which are incorporated by reference.

FIELD OF THE INVENTION

The present invention relates to methods and systems for storing sequencing data.

BACKGROUND

When a couple wants to have children, they may turn to genetic screening to identify if either member is a carrier of a genetic condition. Genetic carrier screening can be done using next-generation sequencing (NGS) technology, which produces a large number of independent reads, each representing anywhere between 10 to 1000 bases of nucleic acid in a person's genome. Nucleic acids are generally sequenced redundantly so that each gene segment is covered a number of times for confidence (i.e., "10× coverage" or "100× coverage"). Thus, a multi-gene genetic screening can produce millions of reads stored in very large sequence read files.

There are considerable challenges involved in storing and transferring the immense amount of sequencing data generated by NGS technologies. In fact, the costs of file storage and transfer may be a bottleneck that poses a significant obstacle to personalized medicine (see, e.g., Deorowicz, 2013, Data compression for sequencing data, Algorithms for Molecular Biology 8:25). Existing methods for compressing sequencing data are not satisfactory because they create binary files that are not human-readable, are lossy, or are inexorably wrapped into other specialized alignment or reference-mapping programs (see Bonfield, 2013, Compression of FASTQ and SAM format sequencing data, PLoS One 8(3):e59190).

SUMMARY

The invention provides systems and methods for compressing sequence read files by identifying duplicative sequence information and storing only unique sequence information. Storing only the unique sequence information reduces the storage space needed and thus also reduces the costs associated with data storage and transfer. Since sets of sequence reads can be stored and transferred using less disk space and less bandwidth for transfers, the sheer volume of data generated by NGS is not a bottleneck that limits the ability of clinics and labs to perform research and services such as genetic carrier screening. Methods of the invention can be lossless and the original sequence reads can be re-created from the compressed data. Additionally, methods of the invention may be implemented in standalone programs not wedded to other analytical applications, thus providing useful compression tools of general applicability. Such a standalone tool can provide results that are consistent and predictable. Further, compressed sequence data may be stored in human-readable text files. Such formats facilitate ready comprehension and also make it easier to work with compressed files—i.e., to write new scripts de novo that extract and analyze sequence reads.

Methods of the invention encompass obtaining a plurality of sequence reads from one or more samples in any suitable file format, identifying sets of duplicative sequence reads, and storing only one read for each set of the duplicative sequence reads. Suitable file formats include the FASTA and FASTQ file formats. FASTA and FASTQ are common file formats used to store raw sequence reads from high throughput sequencing. FASTQ files store an identifier for each sequence read, the sequence, and the quality score string of each read. FASTA files store the identifier and sequence only. These two file formats are the inputs to many common sequencing alignment and assembly algorithms. The invention recognizes that the read sequence information for FASTQ and FASTA files within and across samples tends to be highly redundant or duplicative. This means that many of the sequence reads will consist of the same sequence. Methods of the invention exploit this redundancy to achieve a many-fold reduction in file size, and there is no loss in the retrieval of the stored data. For example, the invention can be used to read the FASTA/FASTQ file associated with a sample and store only the unique read sequences in a master read sequence file.

To produce the compressed set of data, the invention further encompass collecting meta information, such as a read identifier, for each read that has the same sequence as the identified unique sequence. This meta information is then written to a file for that sample in which the meta information is correlated to the unique sequence reads identified in original FASTA/FASTQ file and now stored in a master read sequence file. Because this new file does not contain the duplicative information found in the original file, it is smaller and easier to transfer than the original file. Moreover, the compressed file need not contain any actual sequence data at all. In certain aspects, the compressed file may simply contain the identifier for the sequence read indexed to the unique sequences stored in the master file.

Aspects of the invention provide systems and methods for compressing sequence data. Sequence data is compressed by obtaining—using a computer system comprising a processor coupled to a non-transitory memory—a plurality of sequence reads. Each sequence read includes a sequence string and meta information. The sequence reads may be provided in the format of one or more FASTA or FASTQ files, for example, with the meta information including the description line (preceded by the ">" character) and optionally, in the case of FASTQ, quality scores. The sequence string preferably represents nucleotide sequence data, e.g., using IUPAC nucleotide codes. A subset of the sequence strings that contains only unique entries is identified. Systems and methods of the invention may then be used to write output that includes the identified subset and—for each of the plurality of sequence reads—the meta information for that sequence read with an indicator of the unique entry in the subset that represents that sequence read.

In some embodiments, the subset (i.e., containing only unique sequence reads) is written to a master reads file, which may be a text file. Preferably, the unique sequence reads are represented in the master reads file using IUPAC nucleotide codes so that the files are human-readable and further processing (e.g., using a scripting language such as Perl or Python) can be easily performed. The meta information may be written to compressed output files corresponding to the input FASTA or FASTQ files.

Methods can include reconstituting the original input from only the output and in certain embodiments the retrieval is lossless, even perfectly lossless. That is, the output may be processed to create new FASTA or FASTQ files comprising the plurality of sequence reads. Where the retrieval is lossless, the new FASTA or FASTQ files contain the same information as the FASTA or FASTQ files.

As shown herein, methods and systems of the invention provide significant reductions in file sizes and thus in amounts of disk-space required to store sequence reads or the amounts of bandwidth required to transmit sequence reads. In some embodiments, the output of compression according to methods of the invention occupies less than 25% of the disk space required to store the obtained plurality of sequence reads. The output may be found to occupy on the order of 10% of the disk space required to store the obtained plurality of sequence reads.

Certain aspects of the invention are especially amenable for implementation using a computer system. The computer system is able to store sequence information in such a way that the storage of any duplicative sequence information is avoided. Such systems generally include a central processing unit (CPU) and storage coupled to the CPU. The storage is one or more non-transitory, computer-readable media that contain instructions that when executed by the CPU, cause the system to obtain a plurality of sequence reads from the sample, identify one or more sets of duplicative sequence reads within that plurality, and store only one of the sequence reads from each set of the duplicative sequence reads. The storage may also contain instructions that cause the computer to produce a compressed file of sequence information containing meta information associated with the individual sequence reads correlated to the unique sequence reads stored in a master read file.

The invention also encompasses systems for practicing the invention. A system of the invention can include a sequencer for sequencing a nucleic acid to generate at least one sequence read, a computer for identifying sets of duplicative reads and storing a single sequence read from each set of duplicative sequence reads, and a database for storing a master file consisting of the single sequences saved from each set of duplicative sequence reads.

The invention is amenable with any suitable type of data file. In addition to the aforementioned FASTA and FASTQ files, sequence reads can also be captured in Variant Call Format (VCF) files. With advances in high throughput sequencing, it is common for multiple sequencing centers to detect variants in the human genome and report them through these VCF files. The invention can facilitate the development of a unified database to store variant information in VCF files from different sources in a way that allows researchers to perform complex allele-, sample-, and population-level queries across centers. The unified database can consolidate variant information in the VCF files from different samples by storing every unique allele (e.g. unique sequence read) on one universal allele table and by storing references of these unique alleles to associated samples and sample-level metadata.

In certain aspects, the invention provides a system for storing for storing sequence read data. The system includes a processor coupled to a non-transitory memory containing instructions executable by the processor to cause the system to: obtain input file comprising a plurality of sequence reads, identify one or more sets of duplicative sequence reads within the plurality of sequence reads, and store only one of the sequence reads from each of the one or more sets of duplicative sequence reads. The system may further include a nucleic acid sequencing instrument connected to the system. Preferably, the system is operable to store the only one of the sequence reads from each of the one or more sets of duplicative reads in a text file using IUPAC nucleotide characters. Preferably, the system output is stored as plain text (e.g., and may be opened using a text editor program and read on-screen by a person). In certain embodiments, the instructions executable by the processor are provided as a standalone program (i.e., that performs the recited steps and do not also perform other bioinformatics analysis). In a preferred embodiment, the sequence read data is stored without loss.

Aspects of the invention provide a method for compressing sequence data. The method includes: obtaining—using a computer system comprising a processor coupled to a non-transitory memory—a plurality of sequence reads, each sequence read comprising a sequence string and meta information; identifying a subset of the sequence strings that contains only unique entries; writing output comprising the subset and—for each of the plurality of sequence reads—the meta information for that sequence read with an indicator of the unique entry in the subset that represents that sequence read. Preferably the output comprises one or more text files that store the subset using IUPAC nucleotide codes. Preferably, the output is stored as plain text (e.g., and may be opened using a text editor program and read on-screen by a person). In a preferred embodiment, the sequence read data is stored without loss. The method may include processing the output to create new FASTA or FASTQ files comprising the plurality of sequence reads. The plurality of sequence reads may be obtained as FASTA or FASTQ files and the new FASTA or FASTQ files may contain the same information as the FASTA or FASTQ files. In some embodiments, the output occupies less than % of the disk space required to store the obtained plurality of sequence reads.

BRIEF DESCRIPTION OF THE DRAWINGS

FIG. 1 depicts sequence data for two samples.

FIG. 3 shows an example master reads file.

DETAILED DESCRIPTION

Figure 2:
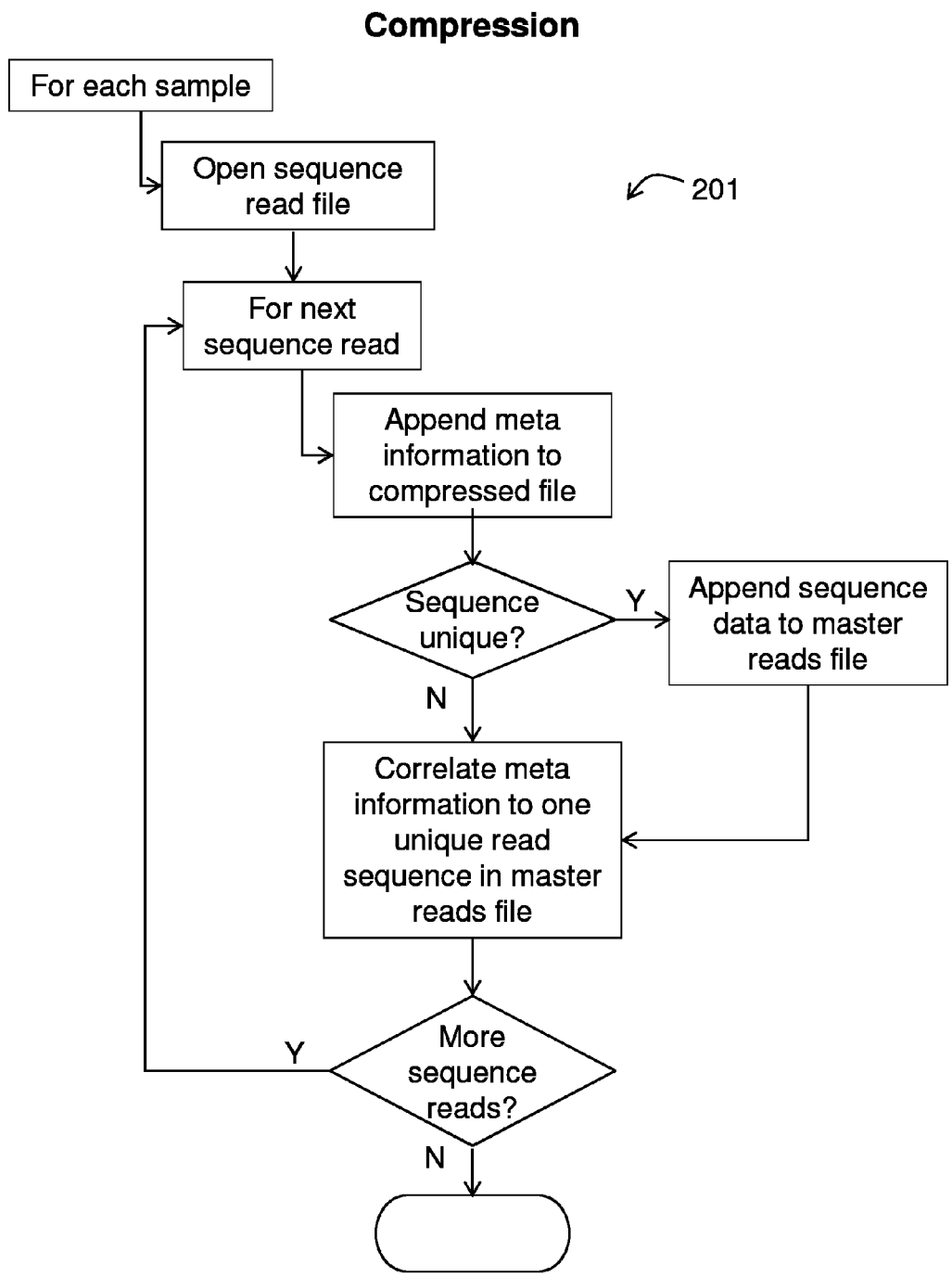
FIG. 2 diagrams an algorithm for compression and storage of sequence read data.

The invention generally relates to storing sequence read data. The invention can involve obtaining a plurality of sequence reads from a sample, identifying one or more sets of duplicative sequence reads within that plurality, and storing only one of the sequence reads from each set of the duplicative sequence reads. The invention also encompasses computers and systems for implementing the provided methods.

General methods for obtaining samples, generating sequencing reads, and various types of sequencing useful for practicing the invention will now be described. It is to be understood that these exemplary methods are not limiting and may be modified as necessary by those skilled in the art.

Obtaining a plurality of sequence reads can include sequencing a nucleic acid from a sample to generate the sequence reads. As explained in detail below, obtaining a plurality of sequence reads can also include receiving sequencing data from a sequencer. Nucleic acid in a sample can be any nucleic acid, including for example, genomic DNA in a tissue sample, cDNA amplified from a particular target in a laboratory sample, or mixed DNA from multiple organisms. In some embodiments, the sample includes homozygous DNA from a haploid or diploid organism. For example, a sample can include genomic DNA from a patient who is homozygous for a rare recessive allele. In other embodiments, the sample includes heterozygous genetic material from a diploid or polyploidy organism with a somatic mutation such that two related nucleic acids are present in allele frequencies other than 50 or 100%, i.e., 20%, 5%, 1%, 0.1%, or any other allele frequency.

In one embodiment, nucleic acid template molecules (e.g., DNA or RNA) are isolated from a biological sample containing a variety of other components, such as proteins, lipids, and non-template nucleic acids. Nucleic acid template molecules can be obtained from any cellular material, obtained from animal, plant, bacterium, fungus, or any other cellular organism. Biological samples for use in the present invention also include viral particles or preparations. Nucleic acid template molecules can be obtained directly from an organism or from a biological sample obtained from an organism, e.g., from blood, urine, cerebrospinal fluid, seminal fluid, saliva, sputum, stool, and tissue. Any tissue or body fluid specimen (e.g., a human tissue of bodily fluid specimen) may be used as a source for nucleic acid to use in the invention. Nucleic acid template molecules can also be isolated from cultured cells, such as a primary cell culture or cell line. The cells or tissues from which template nucleic acids are obtained can be infected with a virus or other intracellular pathogen. A sample can also be total RNA extracted from a biological specimen, a cDNA library, viral, or genomic DNA. A sample may also be isolated DNA from a non-cellular origin, e.g. amplified/isolated DNA from the freezer.

Generally, nucleic acid can be extracted, isolated, amplified, or analyzed by a variety of techniques such as those described by Green and Sambrook, Molecular Cloning: A Laboratory Manual (Fourth Edition), Cold Spring Harbor Laboratory Press, Woodbury, N.Y. 2,028 pages (2012); or as described in U.S. Pat. No. 7,957,913; U.S. Pat. No. 7,776,616; U.S. Pat. No. 5,234,809; U.S. Pub. 2010/0285578; and U.S. Pub. 2002/0190663.

Nucleic acid obtained from biological samples may be fragmented to produce suitable fragments for analysis. Template nucleic acids may be fragmented or sheared to a desired length, using a variety of mechanical, chemical, and/or enzymatic methods. DNA may be randomly sheared via sonication using, for example, an ultrasonicator sold by Covaris (Woburn, Mass.), brief exposure to a DNase, or using a mixture of one or more restriction enzymes, or a transposase or nicking enzyme. RNA may be fragmented by brief exposure to an RNase, heat plus magnesium, or by shearing. The RNA may be converted to cDNA. If fragmentation is employed, the RNA may be converted to cDNA before or after fragmentation. In one embodiment, nucleic acid is fragmented by sonication. In another embodiment, nucleic acid is fragmented by a hydroshear instrument. Generally, individual nucleic acid template molecules can be from about 2 kb bases to about 40 kb. In a particular embodiment, nucleic acids are about 6 kb-10 kb fragments. Nucleic acid molecules may be single-stranded, double-stranded, or double stranded with single-stranded regions (for example, stem- and loop-structures).

A biological sample may be lysed, homogenized, or fractionated in the presence of a detergent or surfactant as needed. Suitable detergents may include an ionic detergent (e.g., sodium dodecyl sulfate or N-lauroylsarcosine) or a nonionic detergent (such as the polysorbate 80 sold under the trademark TWEEN by Uniqema Americas (Paterson, N.J.) or $C_{14}H_{22}O(C_2H_4)_n$, known as TRITON X-100). Once a nucleic acid is extracted or isolated from the sample it may be amplified.

Amplification refers to production of additional copies of a nucleic acid sequence and is generally carried out using polymerase chain reaction (PCR) or other technologies known in the art. The amplification reaction may be any amplification reaction known in the art that amplifies nucleic acid molecules such as PCR. Other amplification reactions include nested PCR, PCR-single strand conformation polymorphism, ligase chain reaction, strand displacement amplification and restriction fragments length polymorphism, transcription based amplification system, rolling circle amplification, and hyper-branched rolling circle amplification, quantitative PCR, quantitative fluorescent PCR (QF-PCR), multiplex fluorescent PCR (MF-PCR), real time PCR (RTPCR), restriction fragment length polymorphism PCR (PCR-RFLP), in situ rolling circle amplification (RCA), bridge PCR, picotiter PCR, emulsion PCR, transcription amplification, self-sustained sequence replication, consensus sequence primed PCR, arbitrarily primed PCR, degenerate oligonucleotide-primed PCR, and nucleic acid based sequence amplification (NABSA). Amplification methods that can be used include those described in U.S. Pat. Nos. 5,242,794; 5,494,810; 4,988,617; and 6,582,938. In certain embodiments, the amplification reaction is PCR as described, for example, U.S. Pat. No. 4,683,195; and U.S. Pat. No. 4,683,202, hereby incorporated by reference. Primers for PCR, sequencing, and other methods can be prepared by cloning, direct chemical synthesis, and other methods known in the art. Primers can also be obtained from commercial sources such as Eurofins MWG Operon (Huntsville, Ala.) or Life Technologies (Carlsbad, Calif.).

Amplification adapters may be attached to the fragmented nucleic acid. Adapters may be commercially obtained, such as from Integrated DNA Technologies (Coralville, Iowa). In certain embodiments, the adapter sequences are attached to the template nucleic acid molecule with an enzyme. The enzyme may be a ligase or a polymerase. The ligase may be any enzyme capable of ligating an oligonucleotide (RNA or DNA) to the template nucleic acid molecule. Suitable ligases include T4 DNA ligase and T4 RNA ligase, available commercially from New England Biolabs (Ipswich, Mass.). Methods for using ligases are well known in the art. The polymerase may be any enzyme capable of adding nucleotides to the 3' and the 5' terminus of template nucleic acid molecules.

The ligation may be blunt ended or utilize complementary overhanging ends. In certain embodiments, the ends of the fragments may be repaired, trimmed (e.g. using an exonuclease), or filled (e.g., using a polymerase and dNTPs) following fragmentation to form blunt ends. In some embodiments, end repair is performed to generate blunt end 5' phosphorylated nucleic acid ends using commercial kits, such as those available from Epicentre Biotechnologies (Madison, Wis.). Upon generating blunt ends, the ends may be treated with a polymerase and dATP to form a template independent addition to the 3'-end and the 5'-end of the fragments, thus producing a single A overhanging. This single A is used to guide ligation of fragments with a single T overhanging from the 5'-end in a method referred to as T-A cloning. Alternatively, because the possible combination of overhangs left by the restriction enzymes are known after a restriction digestion, the ends may be left as-is, i.e., ragged ends. In certain embodiments double stranded oligonucleotides with complementary overhanging ends are used.

Embodiments of the invention involve attaching the bar code sequences to the template nucleic acids. In certain embodiments, a bar code is attached to each fragment. In other embodiments, a plurality of bar codes, e.g., two bar codes, are attached to each fragment. A bar code sequence generally includes certain features that make the sequence useful in sequencing reactions. For example the bar code sequences are designed to have minimal or no homo-polymer regions, i.e., 2 or more of the same base in a row such as AA or CCC, within the bar code sequence. The bar code sequences are also designed so that they are at least one edit distance away from the base addition order when performing base-by-base sequencing, ensuring that the first and last base do not match the expected bases of the sequence.

The bar code sequences are designed such that each sequence is correlated to a particular portion of nucleic acid, allowing sequence reads to be correlated back to the portion from which they came. Methods of designing sets of bar code sequences are shown for example in U.S. Pat. No. 6,235,475, the contents of which are incorporated by reference herein in their entirety. In certain embodiments, the bar code sequences range from about 5 nucleotides to about 15 nucleotides. In a particular embodiment, the bar code sequences range from about 4 nucleotides to about 7 nucleotides. Since the bar code sequence is sequenced along with the template nucleic acid, the oligonucleotide length should be of minimal length so as to permit the longest read from the template nucleic acid attached. Generally, the bar code sequences are spaced from the template nucleic acid molecule by at least one base (minimizes homo-polymeric combinations). In certain embodiments, the bar code sequences are attached to the template nucleic acid molecule, e.g., with an enzyme. The enzyme may be a ligase or a polymerase, as discussed below. Attaching bar code sequences to nucleic acid templates is shown in U.S. Pub. 2008/0081330 and U.S. Pub. 2011/0301042, the contents of which are incorporated by reference herein in its entirety. Methods for designing sets of bar code sequences and other methods for attaching bar code sequences are shown in U.S. Pat. Nos. 7,544,473; 7,537,897; 7,393,665; 6,352,828; 6,172,218; 6,172,214; 6,150,516; 6,138,077; 5,863,722; 5,846,719; 5,695,934; and 5,604,097, each incorporated by reference.

Amplification or sequencing adapters or barcodes, or a combination thereof, may be attached to the fragmented nucleic acid. Such molecules may be commercially obtained, such as from Integrated DNA Technologies (Coralville, Iowa). In certain embodiments, such sequences are attached to the template nucleic acid molecule with an enzyme such as a ligase. Suitable ligases include T4 DNA ligase and T4 RNA ligase, available commercially from New England Biolabs (Ipswich, Mass.). The ligation may be blunt ended or via use of complementary overhanging ends. In certain embodiments, following fragmentation, the ends of the fragments may be repaired, trimmed (e.g. using an exonuclease), or filled (e.g., using a polymerase and dNTPs) to form blunt ends. In some embodiments, end repair is performed to generate blunt end 5' phosphorylated nucleic acid ends using commercial kits, such as those available from Epicentre Biotechnologies (Madison, Wis.). Upon generating blunt ends, the ends may be treated with a polymerase and dATP to form a template independent addition to the 3'-end and the 5'-end of the fragments, thus producing a single A overhanging. This single A can guide ligation of fragments with a single T overhanging from the 5'-end in a method referred to as T-A cloning. Alternatively, because the possible combination of overhangs left by the restriction enzymes are known after a restriction digestion, the ends may be left as-is, i.e., ragged ends. In certain embodiments double stranded oligonucleotides with complementary overhanging ends are used.

After any processing steps (e.g., obtaining, isolating, fragmenting, amplification, or barcoding), nucleic acid can be sequenced.

Sequencing may be by any method known in the art. DNA sequencing techniques include classic dideoxy sequencing reactions (Sanger method) using labeled terminators or primers and gel separation in slab or capillary, sequencing by synthesis using reversibly terminated labeled nucleotides, pyrosequencing, 454 sequencing, Illumina/Solexa sequencing, allele specific hybridization to a library of labeled oligonucleotide probes, sequencing by synthesis using allele specific hybridization to a library of labeled clones that is followed by ligation, real time monitoring of the incorporation of labeled nucleotides during a polymerization step, polony sequencing, and SOLiD sequencing. Sequencing of separated molecules has more recently been demonstrated by sequential or single extension reactions using polymerases or ligases as well as by single or sequential differential hybridizations with libraries of probes.

A sequencing technique that can be used includes, for example, use of sequencing-by-synthesis systems sold under the trademarks GS JUNIOR, GS FLX+ and 454 SEQUENCING by 454 Life Sciences, a Roche company (Branford, Conn.), and described by Margulies, M. et al., Genome sequencing in micro-fabricated high-density picotiter reactors, Nature, 437:376-380 (2005); U.S. Pat. No. 5,583,024; U.S. Pat. No. 5,674,713; and U.S. Pat. No. 5,700,673, the contents of which are incorporated by reference herein in their entirety. 454 sequencing involves two steps. In the first step of those systems, DNA is sheared into fragments of approximately 300-800 base pairs, and the fragments are blunt ended. Oligonucleotide adaptors are then ligated to the ends of the fragments. The adaptors serve as primers for amplification and sequencing of the fragments. The fragments can be attached to DNA capture beads, e.g., streptavidin-coated beads using, e.g., Adaptor B, which contains 5'-biotin tag. The fragments attached to the beads are PCR amplified within droplets of an oil-water emulsion. The result is multiple copies of clonally amplified DNA fragments on each bead. In the second step, the beads are captured in wells (pico-liter sized). Pyrosequencing is performed on each DNA fragment in parallel. Addition of one or more nucleotides generates a light signal that is recorded by a CCD camera in a sequencing instrument. The signal strength is proportional to the number of nucleotides incorporated. Pyrosequencing makes use of pyrophosphate (PPi) which is released upon nucleotide addition. PPi is converted to ATP by ATP sulfurylase in the presence of adenosine 5' phosphosulfate. Luciferase uses ATP to convert luciferin to oxyluciferin, and this reaction generates light that is detected and analyzed.

Another example of a DNA sequencing technique that can be used is SOLiD technology by Applied Biosystems from Life Technologies Corporation (Carlsbad, Calif.). In SOLiD sequencing, genomic DNA is sheared into fragments, and adaptors are attached to the 5' and 3' ends of the fragments to generate a fragment library. Alternatively, internal adaptors can be introduced by ligating adaptors to the 5' and 3' ends of the fragments, circularizing the fragments, digesting the circularized fragment to generate an internal adaptor, and attaching adaptors to the 5' and 3' ends of the resulting fragments to generate a mate-paired library. Next, clonal bead populations are prepared in microreactors containing beads, primers, template, and PCR components. Following PCR, the templates are denatured and beads are enriched to separate the beads with extended templates. Templates on the selected beads are subjected to a 3' modification that permits bonding to a glass slide. The sequence can be determined by sequential hybridization and ligation of partially random oligonucleotides with a central determined base (or pair of bases) that is identified by a specific fluorophore. After a color is recorded, the ligated oligonucleotide is removed and the process is then repeated.

Another example of a DNA sequencing technique that can be used is ion semiconductor sequencing using, for example, a system sold under the trademark ION TORRENT by Ion Torrent by Life Technologies (South San Francisco, Calif.). Ion semiconductor sequencing is described, for example, in Rothberg, et al., An integrated semiconductor device enabling non-optical genome sequencing, Nature 475:348-352 (2011); U.S. Pub. 2010/0304982; U.S. Pub. 2010/0301398; U.S. Pub. 2010/0300895; U.S. Pub. 2010/0300559; and U.S. Pub. 2009/0026082, the contents of each of which are incorporated by reference in their entirety.

Another example of a sequencing technology that can be used is Illumina sequencing. Illumina sequencing is based on the amplification of DNA on a solid surface using fold-back PCR and anchored primers. Genomic DNA is fragmented, and adapters are added to the 5' and 3' ends of the fragments. DNA fragments that are attached to the surface of flow cell channels are extended and bridge amplified. The fragments become double stranded, and the double stranded molecules are denatured. Multiple cycles of the solid-phase amplification followed by denaturation can create several million clusters of approximately 1,000 copies of single-stranded DNA molecules of the same template in each channel of the flow cell. Primers, DNA polymerase and four fluorophore-labeled, reversibly terminating nucleotides are used to perform sequential sequencing. After nucleotide incorporation, a laser is used to excite the fluorophores, and an image is captured and the identity of the first base is recorded. The 3' terminators and fluorophores from each incorporated base are removed and the incorporation, detection and identification steps are repeated. Sequencing according to this technology is described in U.S. Pat. No. 7,960,120; U.S. Pat. No. 7,835,871; U.S. Pat. No. 7,232,656; U.S. Pat. No. 7,598,035; U.S. Pat. No. 6,911,345; U.S. Pat. No. 6,833,246; U.S. Pat. No. 6,828,100; U.S. Pat. No. 6,306,597; U.S. Pat. No. 6,210,891; U.S. Pub. 2011/0009278; U.S. Pub. 2007/0114362; U.S. Pub. 2006/0292611; and U.S. Pub. 2006/0024681, each of which are incorporated by reference in their entirety.

Another example of a sequencing technology that can be used includes the single molecule, real-time (SMRT) technology of Pacific Biosciences (Menlo Park, Calif.). In SMRT, each of the four DNA bases is attached to one of four different fluorescent dyes. These dyes are phospholinked. A single DNA polymerase is immobilized with a single molecule of template single stranded DNA at the bottom of a zero-mode waveguide (ZMW). It takes several milliseconds to incorporate a nucleotide into a growing strand. During this time, the fluorescent label is excited and produces a fluorescent signal, and the fluorescent tag is cleaved off. Detection of the corresponding fluorescence of the dye indicates which base was incorporated. The process is repeated.

Another example of a sequencing technique that can be used is nanopore sequencing (Soni & Meller, 2007, Progress toward ultrafast DNA sequence using solid-state nanopores, Clin Chem 53(11):1996-2001). A nanopore is a small hole, of the order of 1 nanometer in diameter. Immersion of a nanopore in a conducting fluid and application of a potential across it results in a slight electrical current due to conduction of ions through the nanopore. The amount of current which flows is sensitive to the size of the nanopore. As a DNA molecule passes through a nanopore, each nucleotide on the DNA molecule obstructs the nanopore to a different degree. Thus, the change in the current passing through the nanopore as the DNA molecule passes through the nanopore represents a reading of the DNA sequence.

Another example of a sequencing technique that can be used involves using a chemical-sensitive field effect transistor (chemFET) array to sequence DNA (for example, as described in U.S. Pub. 2009/0026082). In one example of the technique, DNA molecules can be placed into reaction chambers, and the template molecules can be hybridized to a sequencing primer bound to a polymerase. Incorporation of one or more triphosphates into a new nucleic acid strand at the 3' end of the sequencing primer can be detected by a change in current by a chemFET. An array can have multiple chemFET sensors. In another example, single nucleic acids can be attached to beads, and the nucleic acids can be amplified on the bead, and the individual beads can be transferred to individual reaction chambers on a chemFET array, with each chamber having a chemFET sensor, and the nucleic acids can be sequenced.

Another example of a sequencing technique that can be used involves using an electron microscope as described, for example, by Moudrianakis, E. N. and Beer M., in Base sequence determination in nucleic acids with the electron microscope, III. Chemistry and microscopy of guanine-labeled DNA, PNAS 53:564-71 (1965). In one example of the technique, individual DNA molecules are labeled using metallic labels that are distinguishable using an electron microscope. These molecules are then stretched on a flat surface and imaged using an electron microscope to measure sequences.

Sequencing according to embodiments of the invention generates a plurality of reads. Reads according to the invention generally include sequences of nucleotide data less than about 150 bases in length, or less than about 90 bases in length. In certain embodiments, reads are between about 80 and about 90 bases, e.g., about 85 bases in length. In some embodiments, methods of the invention are applied to very short reads, i.e., less than about 50 or about 30 bases in length. Sequence read data can include the sequence data as well as meta information. Sequence read data can be stored in any suitable file format including, for example, VCF files, FASTA files or FASTQ files, as are known to those of skill in the art.

FASTA is originally a computer program for searching sequence databases and the name FASTA has come to also refer to a standard file format. See Pearson & Lipman, 1988, Improved tools for biological sequence comparison, PNAS 85:2444-2448. A sequence in FASTA format begins with a single-line description, followed by lines of sequence data. The description line is distinguished from the sequence data by a greater-than (">") symbol in the first column. The word following the ">" symbol is the identifier of the sequence, and the rest of the line is the description (both are optional). There should be no space between the ">" and the first letter of the identifier. It is recommended that all lines of text be shorter than 80 characters. The sequence ends if another line starting with a ">" appears; this indicates the start of another sequence.

The FASTQ format is a text-based format for storing both a biological sequence (usually nucleotide sequence) and its corresponding quality scores. It is similar to the FASTA format but with quality scores following the sequence data. Both the sequence letter and quality score are encoded with a single ASCII character for brevity. The FASTQ format is a de facto standard for storing the output of high throughput sequencing instruments such as the Illumina Genome Analyzer. Cock et al., 2009, The Sanger FASTQ file format for sequences with quality scores, and the Solexa/Illumina FASTQ variants, Nucleic Acids Res 38(6):1767-1771.

For FASTA and FASTQ files, meta information includes the description line and not the lines of sequence data. In some embodiments, for FASTQ files, the meta information includes the quality scores. For FASTA and FASTQ files, the sequence data begins after the description line and is present typically using some subset of IUPAC ambiguity codes optionally with "–". In a preferred embodiment, the sequence data will use the A, T, C, G, and N characters, optionally including "–" or U as-needed (e.g., to represent gaps or uracil).

As discussed above and elsewhere, the volume of output of NGS instruments is increasing. See, e.g., Pinho & Pratas, 2013, MFCompress: a compression tool for FASTA and multi-FASTA data, Bioinformatics 30(1):117-8; Deorowicz & Grabowski, 2013, Data compression for sequencing data, Alg Mol Bio 8:25; Balzer et al., 2013, Filtering duplicate reads from 454 pyrosequencing data, Bioinformatics 29(7): 830-836; Xu et al., 2012, FastUniq: A fast de novo duplicates removal tool for paired short reads, PLoS One 7(12):e52249; Bonfield and Mahoney, 2013, Compression of FASTQ and SAM format sequencing data, PLoS One 8(3):e59190; and Veeneman et al., 2012, Oculus: faster sequence alignment by streaming read compression, BMC Bioinformatics 13:297. The amount of data generated by NGS technologies raises challenges in storing and transferring files containing such sequencing information. Accordingly, methods and systems of the invention can be used for storing information such as the large volumes of sequence data contained in FASTA or FASTQ files (FASTA/Q files) originating from nucleic acid sequencing technologies.

FIG. 1 depicts two samples in which the sequence data has been stored as FASTA files (Sample1.fa and Sample2.fa). As shown in FIG. 1, each line that begins with an ">" is a description or identifier label and is followed by sequence data (e.g., "Read 1" and "ACGATCC," respectively). The invention recognizes that the read sequence information within and across samples tends to be highly redundant or duplicative. For example, Read 1 and Read 2 of Sample1.fa have identical sequences. Methods of the invention exploit this redundancy to achieve a many-fold reduction in file size and the lossless retrieval in data. This reduction in file size can be performed using an algorithm which identifies one or more sets of duplicative sequence reads within the plurality of sequence reads and stores one only one of the sequence reads from each set of duplicative reads.

FIG. 2 diagrams an algorithm 201 for compression and storage of sequence read data. Of course, the exact algorithm can be developed as necessary as determined by those skilled in the art. Methods and systems of the invention can be applied to any number of sources or sample and is illustrated here as though a plurality of samples provide the inputs and each sample is represented by one FASTA/Q file. It will be recognized that each sample may have one or any number of FASTA/Q files.

For each sample, the method includes opening and reading the FASTA/Q file. A first or next one of the sequence reads is examined. For that read in the open FASTA/Q file, the meta information (e.g. read ID or description, base qualities, etc.) is collected. For that read, any meta information is appended into a new "compressed file" corresponding to the opened FASTA/Q file.

For that read, the sequence data is examined and a determination is made whether that sequence data is unique or if it is already represented in a master reads file. If the sequence is unique, the unique read sequence is stored in a master read sequence file. In a preferred embodiment, the unique read sequence is stored in the master read sequence file using conventional IUPAC nucleotide characters such as the IUPAC ambiguity codes or preferably A, T, C, G, N, and optionally "–", U, or both. To use IUPAC nucleotide characters means that characters such as A, T, C, G, N, or U are used while also optionally using other characters such as "–", "?", "$" or any other characters or whitespace. Since the reads are stored using conventional characters, not only are the resultant files human-readable, it is very easy to computer programs to be written to process the contents of those file (e.g., a practitioner can work with the compressed files using a high-level scripting language such as Perl or Python—see generally Dudley & Butte, 2009, A quick guide for developing effective bioinformatics programming skills, PLoS Comp Biol 5(12): e1000589). For any given read, the meta information in the compressed file is correlated to the one entry in the master read sequence file that matches that read.

A correlation between an entry in the compressed file and an entry in the master reads file can be recorded in any suitable way. For example, it may be assumed that entries in the master reads file are indexed by their ordinal position. Thus, the first entry could be referred to by the index "1", the second entry referred to by the index "2", and so on. The index may be written into the compressed file in the stead of the sequence data.

After the entry in the compressed file is completed (e.g., the meta information is written and the appropriate index is written), a determination is made whether the open FASTA/Q file includes more sequence reads to be compressed. If there are more sequence reads, the methods turns to examining the next one of the sequence reads. If there are no more sequence reads, the examination and writing is complete and the files may be closed (e.g., if Perl is used, the file handle may be closed).

The output of method 201 includes at least one master reads file and at least one compressed file. These may be stored as a single file, if convenient. For example, the first portion of an output file could contain the master reads and a second portion could contain the meta information and indices. In some embodiments, one master reads file is create and one compressed file is created for each sample or each FASTA/Q file used for input.

FIG. 3 shows an example master reads file named MasterReadsFile.txt that includes one entry for each unique sequence reads. Since all of the nucleic acid sequence data is contained in the master reads file, only the meta information for each FASTA/Q file needs to be written to a compressed file for that sample.

As shown in FIG. 3, five unique sequences have been identified from the two sample files shown in FIG. 1. These unique sequences have been stored onto a master read sequence file. In the embodiment depicted in FIG. 3, the master read sequence file is a text file, however, any computer-readable format may be used.

Figure 4:
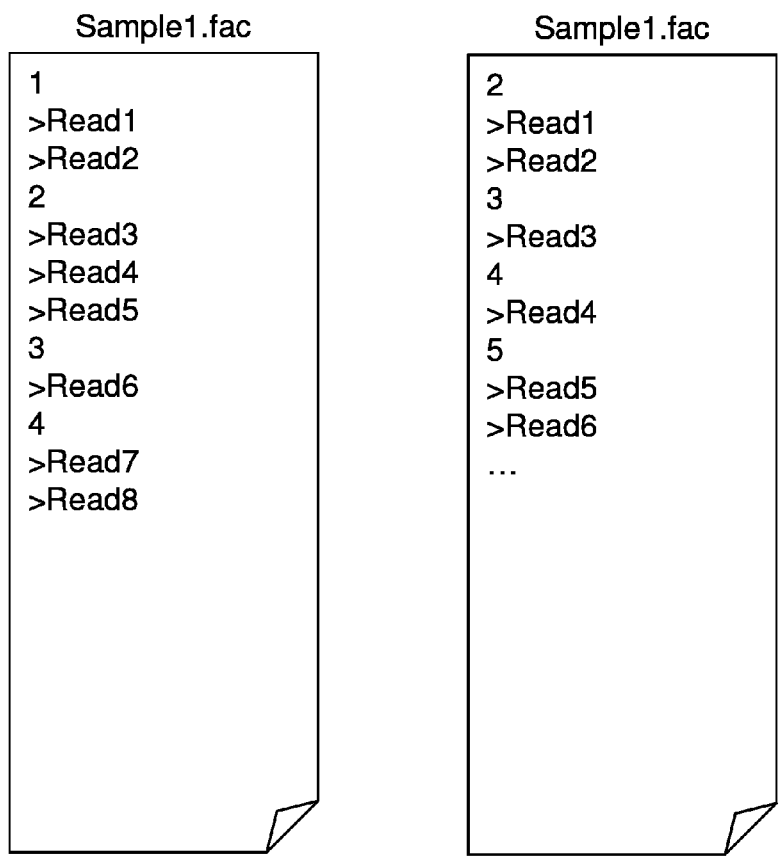
FIG. 4 depicts compressed data sets stored in compressed files.

FIG. 4 depicts compressed data sets stored in compressed files, Sample1.fac and Sample2.fac, which respectively correspond to Sample1.fa and Sample 2.fa of FIG. 1. As shown in FIG. 4, the collected meta information comprised the read IDs associated with the original sequence reads (e.g. Read 1, Read 2, etc.) Each of the read IDs is matched to a unique sequence captured in the master read file. For example, Reads 1 and 2 of Sample1.fac are indexed to the first unique sequence (ACGATCC). Reads 3-5 of Sample1.fac are indexed to the second unique sequence (ACGGTTA). Reads 5 and 6 of Sample2.fac are indexed to the fifth unique sequence (ACAGATT). As shown in FIG. 4, the index is written in the file above the meta information which it corresponds to. This is arbitrary, and one may write the meta information followed by the index. It is additionally noted that the index need not be repeated for each line of meta-information. If two or more consecutive lines of meta information would have the same index, those lines may be grouped (as shown in FIG. 4) and the index given only once (above the groups in FIG. 4)

Because these new files (Sample1.fac and Sample 2.fac) do not contain the duplicative information found in the original files (Sample1.fa and Sample2.fa), they are smaller and easier to transfer than the original files. In addition, the compressed files need not contain any actual sequence data at all. As shown in FIG. 4, the compressed files may simply contain the identifier for the sequence read indexed to the unique sequences stored in the master file.

In some embodiments, the at least one master sequence read file and the output file are stored as plain text files (e.g., using encoding such as ASCII; ISO/IEC 646; EBCDIC; UTF-8; or UTF-16). A computer system provided by the invention may include a text editor program capable of opening the plain text files. A text editor program may refer to a computer program capable of presenting contents of a text file (such as a plain text file) on a computer screen, allowing a human to edit the text (e.g., using a monitor, keyboard, and mouse). Exemplary text editors include, without limit, Microsoft Word, emacs, pico, vi, BBEdit, and TextWrangler. Preferably, the text editor program is capable of displaying the plain text files on a computer screen, showing the meta information and the sequence reads in a human-readable format (e.g., not binary encoded but instead using alphanumeric characters as they would be used in print human writing).

Figure 5:
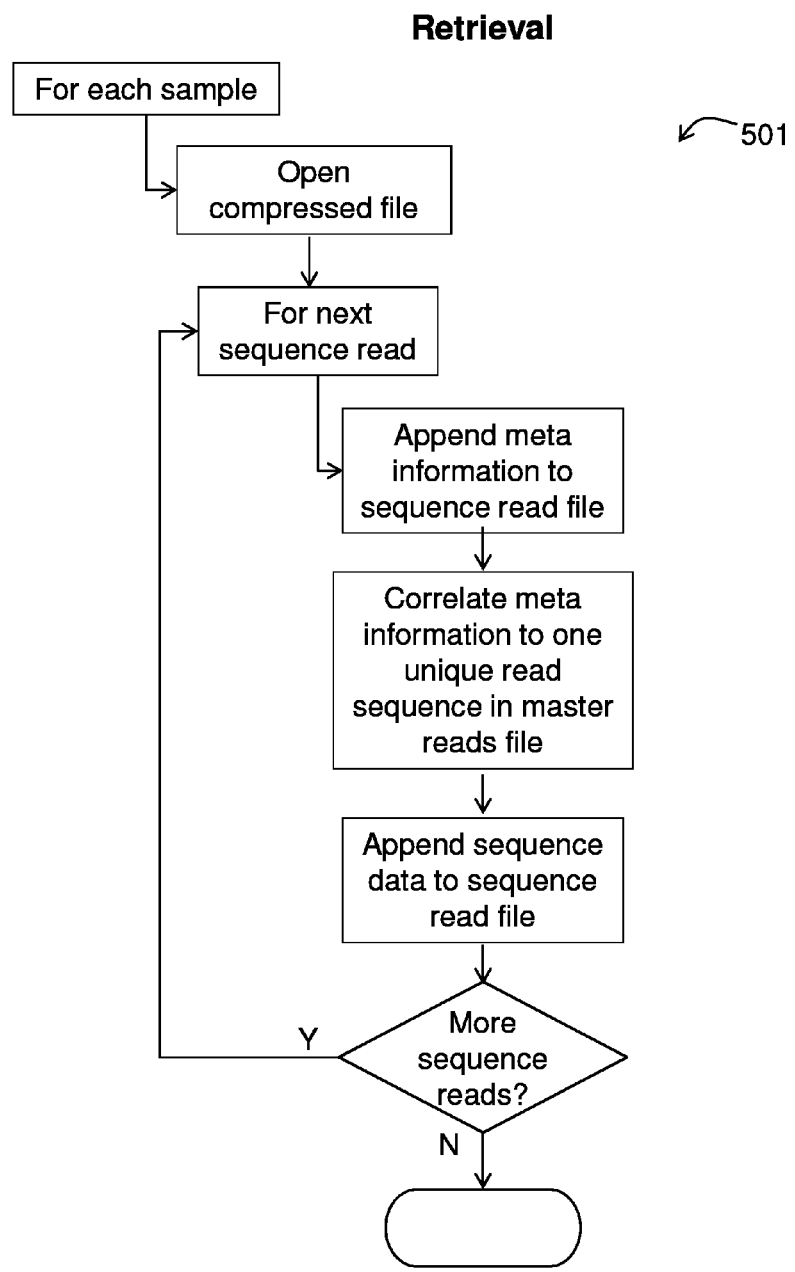
FIG. 5 shows a method for uncompressing original files from compressed data.

FIG. 5 diagrams a method 501 for uncompressing, or retrieving, the original files from the compressed file and the master reads file. Each compressed file is opened and read by the computer (e.g., if Perl is used, a file handle is opened). For each read in the compressed file, the meta information is correlated to the appropriate one unique read in the master reads file. In a sequence read file (i.e., the uncompressed output of retrieval method 501), for each sequence read, the meta information and the sequence data are appended. Since the original input is what is being used, the original files are re-created. Thus if the compressed files were created from FASTA or FASTQ files, retrieval method 501 will create FASTA or FASTQ files. Additionally, the retrieval 501 may be perfectly loss-less. The output may be an exact reproduction of the input.

While methods have been discussed with reference to FASTA or FASTQ files, methods and systems of the invention may be used to compress any suitable sequence file format including, for example, files in the Variant Call Format (VCF) format. A typical VCF file will include a header section and a data section. The header contains an arbitrary number of meta-information lines, each starting with characters '##', and a TAB delimited field definition line starting with a single '#' character. The field definition line names eight mandatory columns and the body section contains lines of data populating the columns defined by the field definition line. The VCF format is described in Danecek et al., 2011, The variant call format and VCFtools, Bioinformatics 27(15):2156-2158. The header section may be treated as the meta information to write to the compressed files and the data section may be treated as the lines, each of which will be stored in a master file only if unique.

Using the methods and systems described herein, sequence read data may be compressed such that storage and transfer of genetic information demands significantly less resources in terms of physical disks or time.

Figure 6:
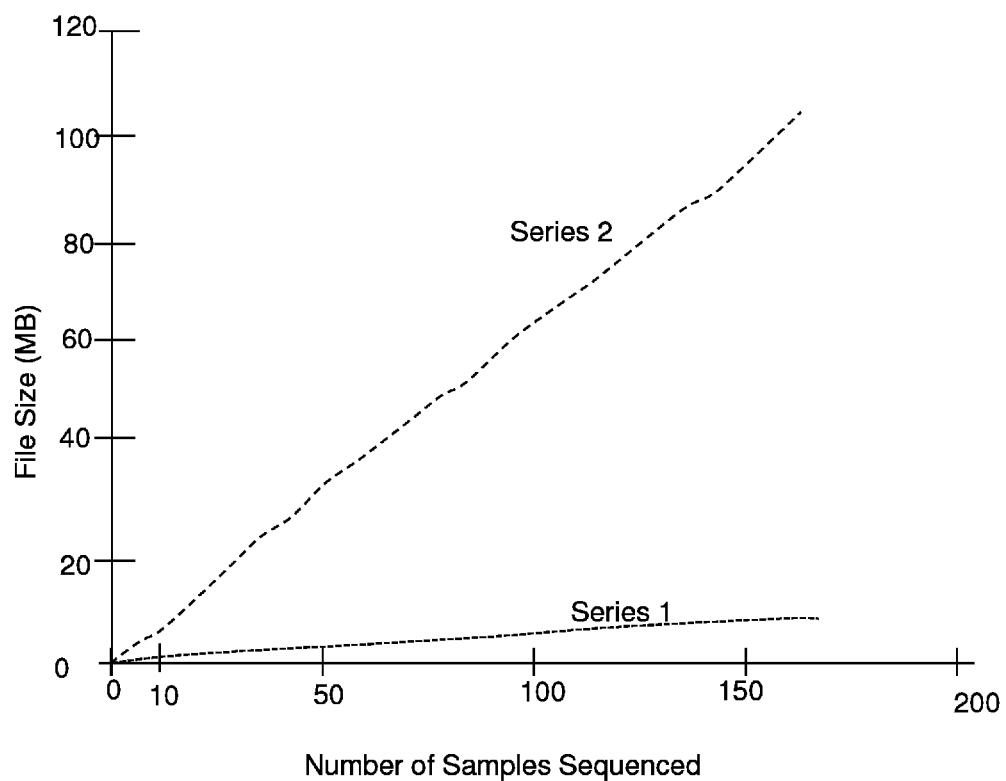
FIG. 6 compares the size of the uncompressed to compressed FASTA files.

FIG. 6 depicts the increase in the size of the uncompressed FASTA files (Series 2) and compressed FASTA files (Series 1) as the number of sampled sequenced increases. As shown, the storage necessary for the compressed files is an order of magnitude less than that required for the uncompressed files. One benefit of methods herein is that they may be used to provide a standalone FASTA/Q compression and decompression program (i.e., a computer tool not married to some other tool or functionality and not a plug-in or wrapper for another program). Use of a standalone program that is agnostic as to other analysis of the sequence reads is beneficial in that compression 201 and retrieval 501 may be implemented at any point without any need for special formatting considerations or without simultaneously performing other analyses on sequence data. Thus a program that performs methods of the invention is versatile in how it may be used within analysis pipelines.

To illustrate, in exemplary pipeline, a sample is obtained, nucleic acids are sequenced and sequence reads are stored in FASTA/Q files. Those FASTA/Q files are then compressed using methods 201 and stored (or optionally transferred to another site). The compressed FASTA/Q files are then de-compressed via retrieval method 501 and the sequence reads are assembled and the original samples are genotyped (e.g., variants are called). Thus it can be seen that where FASTA/Q files that embody a plurality of sequence reads, the output of compression 201 and retrieval 501 of those file is the plurality of sequence reads. The sequence reads may then be further processed or analyzed. Further methods for processing of sequence reads, including the assembly of sequence reads into contigs, is described in detail in U.S. Pat. No. 8,209,130, incorporated herein by reference. A contig, generally, refers to the relationship between or among a plurality of segments of nucleic acid sequences, e.g., reads. Where sequence reads overlap, a contig can be represented as a layered image of overlapping reads.

Certain embodiments of the invention provide for the assembly of sequence reads. In assembly by alignment, for example, the reads are aligned to each other or to a reference. By aligning each read, in turn to a reference genome, all of the reads are positioned in relationship to each other to create the assembly. In addition, aligning or mapping the sequence read to a reference sequence can also be used to identify variant sequences within the sequence read.

Computer programs for assembling reads are known in the art. Such assembly programs can run on a single general-purpose computer, on a cluster or network of computers, or on specialized computing devices dedicated to sequence analysis.

Assembly can be implemented, for example, by the program 'The Short Sequence Assembly by k-mer search and 3' read Extension' (SSAKE), from Canada's Michael Smith Genome Sciences Centre (Vancouver, B.C., CA) (see, e.g., Warren et al., 2007, Assembling millions of short DNA sequences using SSAKE, Bioinformatics, 23:500-501). SSAKE cycles through a table of reads and searches a prefix tree for the longest possible overlap between any two sequences. SSAKE clusters reads into contigs.

Another read assembly program is Forge Genome Assembler, written by Darren Platt and Dirk Evers and available through the SourceForge web site maintained by Geeknet (Fairfax, Va.) (see, e.g., DiGuistini et al., 2009, De novo sequence assembly of a filamentous fungus using Sanger, 454 and Illumina sequence data, Genome Biology, 10:R94). Forge distributes its computational and memory consumption to multiple nodes, if available, and has therefore the potential to assemble large sets of reads. Forge was written in C++ using the parallel MPI library. Forge can handle mixtures of reads, e.g., Sanger, 454, and Illumina reads.

Assembly through multiple sequence alignment can be performed, for example, by the program Clustal Omega, (Sievers et al., 2011, Fast, scalable generation of high-quality protein multiple sequence alignments using Clustal Omega, Mol Syst Biol 7:539), ClustalW, or ClustalX (Larkin et al., 2007, Clustal W and Clustal X version 2.0, Bioinformatics, 23(21):2947-2948) available from University College Dublin (Dublin, Ireland).

Another exemplary read assembly program known in the art is Velvet, available through the web site of the European Bioinformatics Institute (Hinxton, UK) (Zerbino & Birney, Velvet: Algorithms for de novo short read assembly using de Bruijn graphs, Genome Research 18(5):821-829). Velvet implements an approach based on de Bruijn graphs, uses information from read pairs, and implements various error correction steps.

Read assembly can be performed with the programs from the package SOAP, available through the website of Beijing Genomics Institute (Beijing, Conn.) or BGI Americas Corporation (Cambridge, Mass.). For example, the SOAPdenovo program implements a de Bruijn graph approach. SOAP3/GPU aligns short reads to a reference sequence.

Another read assembly program is ABySS, from Canada's Michael Smith Genome Sciences Centre (Vancouver, B.C., CA) (Simpson et al., 2009, ABySS: A parallel assembler for short read sequence data, Genome Res., 19(6):1117-23). ABySS uses the de Bruijn graph approach and runs in a parallel environment.

Read assembly can also be done by Roche's GS De Novo Assembler, known as gsAssembler or Newbler (NEW assemBLER), which is designed to assemble reads from the Roche 454 sequencer (described, e.g., in Kumar & Blaxter, 2010, Comparing de novo assemblers for 454 transcriptome data, Genomics 11:571 and Margulies 2005). Newbler accepts 454 Flx Standard reads and 454 Titanium reads as well as single and paired-end reads and optionally Sanger reads. Newbler is run on Linux, in either 32 bit or 64 bit versions. Newbler can be accessed via a command-line or a Java-based GUI interface.

Cortex, created by Mario Caccamo and Zamin Iqbal at the University of Oxford, is a software framework for genome analysis, including read assembly. Cortex includes cortex_con for consensus genome assembly, used as described in Spanu et al., 2010, Genome expansion and gene loss in powdery mildew fungi reveal tradeoffs in extreme parasitism, Science 330(6010):1543-46. Cortex includes cortex_var for variation and population assembly, described in Iqbal, et al., De novo assembly and genotyping of variants using colored de Bruijn graphs, Nature Genetics 44:226-232, and used as described in Mills et al., 2010, Mapping copy number variation by population-scale genome sequencing, Nature 470:59-65. Cortex is available through the creators' web site and from the SourceForge web site maintained by Geeknet (Fairfax, Va.).

Other read assembly programs include RTG Investigator from Real Time Genomics, Inc. (San Francisco, Calif.); iAssembler (Zheng, et al., 2011, iAssembler: a package for de novo assembly of Roche-454/Sanger transcriptome sequences, BMC Bioinformatics 12:453); TgiCL Assembler (Pertea, et al., Bioinformatics 19(5):651-52 (2003)); Maq (Mapping and Assembly with Qualities) by Heng Li, available for download through the SourceForge website maintained by Geeknet (Fairfax, Va.); MIRA3 (Mimicking Intelligent Read Assembly), described in Chevreux, B., et al., Genome Sequence Assembly Using Trace Signals and Additional Sequence Information, 1999, Computer Science and Biology: Proceedings of the German Conference on Bioinformatics (GCB) 99:45-56; PGA4genomics (described in Zhao F., et al., Genomics. 94(4):284-6 (2009)); and Phrap (described, e.g., in de la Bastide, M. and McCombie, W. R., Current Protocols in Bioinformatics, 17:11.4.1-11.4.15 (2007)). CLC cell is a de Bruijn graph-based computer program for read mapping and de novo assembly of NGS reads available from CLC bio Germany (Muehltal, Germany). Additional discussion of read assembly may be found in Langmead et al., 2009, Ultrafast and memory-efficient alignment of short DNA sequences to the human genome, Genome Biology 10:R25; Horner et al., 2009, BFAST: An alignment tool for large scale genome resequencing, PLoS ONE 4(11): e7767; Li et al., 2009, The Sequence alignment/map (SAM) format and SAMtools, Bioinformatics 25:2078; Lin et al., 2008, ZOOM! Zillions Of Oligos Mapped, Bioinformatics 24:2431; Li & Durbin, 2009, Fast and accurate short read alignment with Burrows-Wheeler Transform, Bioinformatics 25:1754; Li, 2011, Improving SNP discovery by base alignment quality, Bioinformatics 27:1157; and Xu, et al., 2012, FastUniq: A fast de novo duplicates removal tool for paired short reads, PLoS One 7(12):e52249.

In some embodiments, any or all of the steps of the invention are automated. For example, a Perl script or shell script can be written to invoke any of the various programs discussed above (see, e.g., Tisdall, Mastering Perl for Bioinformatics, O'Reilly & Associates, Inc., Sebastopol, Calif. 2003; Michael, R., Mastering Unix Shell Scripting, Wiley Publishing, Inc., Indianapolis, Ind. 2003). Alternatively, methods of the invention may be embodied wholly or partially in one or more dedicated programs, for example, each optionally written in a compiled language such as C++ then compiled and distributed as a binary. Methods of the invention may be implemented wholly or in part as modules within, or by invoking functionality within, existing sequence analysis platforms. In certain embodiments, methods of the invention include a number of steps that are all invoked automatically responsive to a single starting queue (e.g., one or a combination of triggering events sourced from human activity, another computer program, or a machine). Thus, the invention provides methods in which any or the steps or any combination of the steps can occur automatically responsive to a queue. Automatically generally means without intervening human input, influence, or interaction (i.e., responsive only to original or pre-queue human activity).

The invention also encompasses various forms of output, which includes an accurate and sensitive interpretation of the subject nucleic acid. The output of retrieval 501 can be provided in the format of a computer file. In certain embodiments, the output is a FASTA file, FASTQ file, or VCF file. Output may be processed to produce a text file, or an XML file containing sequence data such as a sequence of the nucleic acid aligned to a sequence of the reference genome. In other embodiments, processing yields output containing coordinates or a string describing one or more mutations in the subject nucleic acid relative to the reference genome. Alignment strings known in the art include Simple UnGapped Alignment Report (SUGAR), Verbose Useful Labeled Gapped Alignment Report (VULGAR), and Compact Idiosyncratic Gapped Alignment Report (CIGAR) (Ning, Z., et al., Genome Research 11(10):1725-9 (2001)). These strings are implemented, for example, in the Exonerate sequence alignment software from the European Bioinformatics Institute (Hinxton, UK).

In some embodiments, a sequence alignment is produced—such as, for example, a sequence alignment map (SAM) or binary alignment map (BAM) file—comprising a CIGAR string (the SAM format is described, e.g., in Li, et al., The Sequence Alignment/Map format and SAMtools, Bioinformatics, 2009; 25(16):2078-9). In some embodiments, CIGAR displays or includes gapped alignments one-per-line. CIGAR is a compressed pairwise alignment format reported as a CIGAR string. A CIGAR string is useful for representing long (e.g. genomic) pairwise alignments. A CIGAR string is used in SAM format to represent alignments of reads to a reference genome sequence.

A CIGAR string follows an established motif. Each character is preceded by a number, giving the base counts of the event. Characters used can include M, I, D, N, and S (M=match; I=insertion; D=deletion; N=gap; S=substitution). The CIGAR string defines the sequence of matches/mismatches and deletions (or gaps). For example, the CIGAR string 2MD3M2D2M will mean that the alignment contains 2 matches, 1 deletion (number 1 is omitted in order to save some space), 3 matches, 2 deletions and 2 matches.

As contemplated by the invention, the functions described above can be implemented using a system of the invention that includes software, hardware, firmware, hardwiring, or any combinations of these. Features implementing functions can also be physically located at various positions, including being distributed such that portions of functions are implemented at different physical locations.

As one skilled in the art would recognize as necessary or best-suited for performance of the methods of the invention, a computer system or machines of the invention include one or more processors (e.g., a central processing unit (CPU) a graphics processing unit (GPU) or both), a main memory and a static memory, which communicate with each other via a bus.

Figure 7:
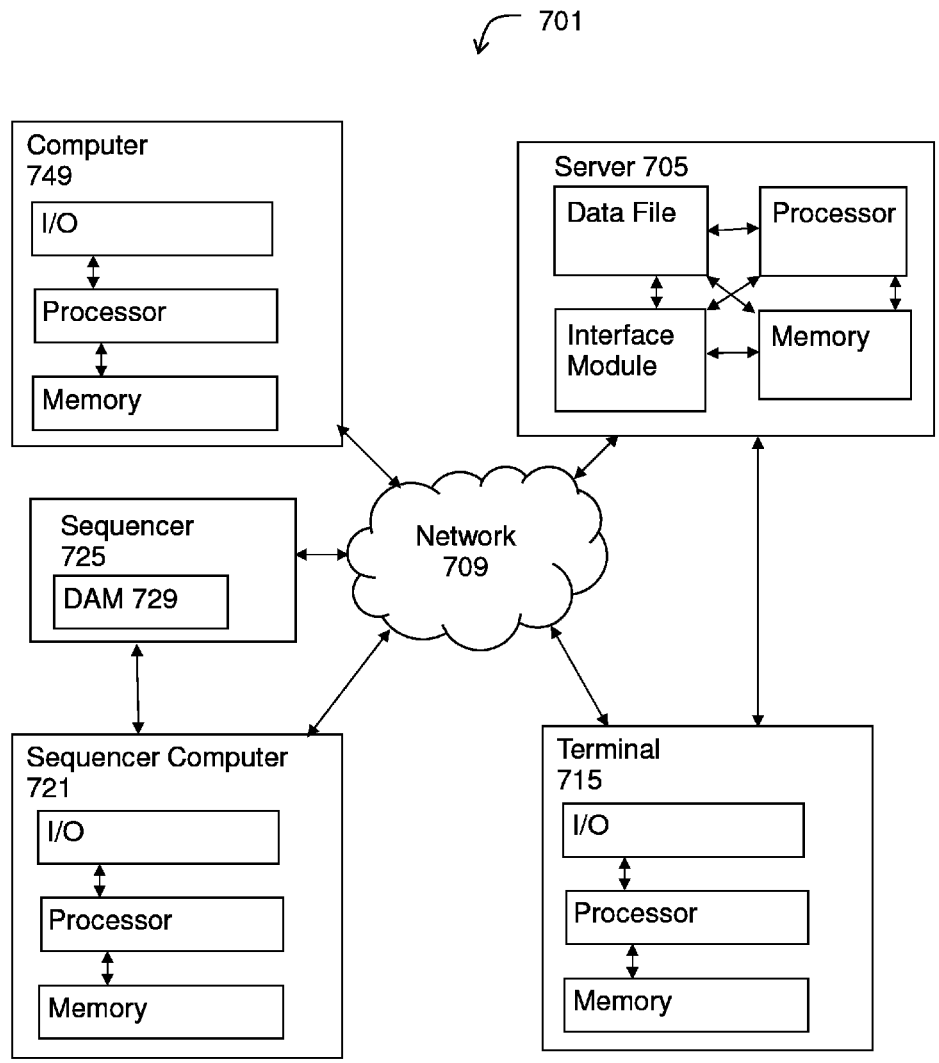
FIG. 7 diagrams a system of the invention.

FIG. 7 diagrams a system 701 suitable for performing methods of the invention. As shown in FIG. 7, system 701 may include one or more of a server computer 705, a terminal 715, a sequencer 715, a sequencer computer 721, a computer 749, or any combination thereof. Each such computer device may communicate via network 709. Sequencer 725 may optionally include or be operably coupled to its own, e.g., dedicated, sequencer computer 721 (including any input/output mechanisms (I/O), processor, and memory). Additionally or alternatively, sequencer 725 may be operably coupled to a server 705 or computer 749 (e.g., laptop, desktop, or tablet) via network 709. Computer 749 includes one or more processor, memory, and I/O. Where methods of the invention employ a client/server architecture, any steps of methods of the invention may be performed using server 705, which includes one or more of processor, memory, and I/O, capable of obtaining data, instructions, etc., or providing results via an interface module or providing results as a file. Server 705 may be engaged over network 709 through computer 749 or terminal 715, or server 705 may be directly connected to terminal 715. Terminal 515 is preferably a computer device. A computer according to the invention preferably includes one or more processor coupled to an I/O mechanism and memory.

A processor may be provided by one or more processors including, for example, one or more of a single core or multi-core processor (e.g., AMD Phenom II X2, Intel Core Duo, AMD Phenom II X4, Intel Core i5, Intel Core i& Extreme Edition 980×, or Intel Xeon E7-2820).

An I/O mechanism may include a video display unit (e.g., a liquid crystal display (LCD) or a cathode ray tube (CRT)), an alphanumeric input device (e.g., a keyboard), a cursor control device (e.g., a mouse), a disk drive unit, a signal generation device (e.g., a speaker), an accelerometer, a microphone, a cellular radio frequency antenna, and a network interface device (e.g., a network interface card (NIC), Wi-Fi card, cellular modem, data jack, Ethernet port, modem jack, HDMI port, mini-HDMI port, USB port), touchscreen (e.g., CRT, LCD, LED, AMOLED, Super AMOLED), pointing device, trackpad, light (e.g., LED), light/image projection device, or a combination thereof.

Memory according to the invention refers to a non-transitory memory which is provided by one or more tangible devices which preferably include one or more machine-readable medium on which is stored one or more sets of instructions (e.g., software) embodying any one or more of the methodologies or functions described herein. The software may also reside, completely or at least partially, within the main memory, processor, or both during execution thereof by a computer within system 501, the main memory and the processor also constituting machine-readable media. The software may further be transmitted or received over a network via the network interface device.

While the machine-readable medium can in an exemplary embodiment be a single medium, the term "machine-readable medium" should be taken to include a single medium or multiple media (e.g., a centralized or distributed database, and/or associated caches and servers) that store the one or more sets of instructions. The term "machine-readable medium" shall also be taken to include any medium that is capable of storing, encoding or carrying a set of instructions for execution by the machine and that cause the machine to perform any one or more of the methodologies of the present invention. Memory may be, for example, one or more of a hard disk drive, solid state drive (SSD), an optical disc, flash memory, zip disk, tape drive, "cloud" storage location, or a combination thereof. In certain embodiments, a device of the invention includes a tangible, non-transitory computer readable medium for memory. Exemplary devices for use as memory include semiconductor memory devices, (e.g., EPROM, EEPROM, solid state drive (SSD), and flash memory devices e.g., SD, micro SD, SDXC, SDIO, SDHC cards); magnetic disks, (e.g., internal hard disks or removable disks); and optical disks (e.g., CD and DVD disks).

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

What is claimed is:

1. A method for storing sequence read data, the method comprising:
obtaining a plurality of sequence reads from a sample;
identifying one or more sets of duplicative sequence reads within the plurality of sequence reads; and
storing only one sequence read from each of the one or more sets of duplicative sequence reads.

2. The method according to claim 1, wherein obtaining the plurality of sequence reads comprises sequencing a nucleic acid from the sample to generate the plurality of sequence reads.

3. The method according to claim 2, wherein sequencing comprises one selected from the group consisting of single molecule sequencing and sequencing by synthesis.

4. The method according claim 1, wherein the sample comprises a human tissue or bodily fluid sample.

5. The method according claim 1, wherein obtaining the plurality of sequence reads comprises obtaining a computer-readable input file.

6. The method according to claim 5, wherein the computer-readable input file is once selected from the group consisting of: a FASTA file; a FASTQ file; and a VCF file.

7. The method according to claim 1, further comprising storing the only one sequence read from each of the one or more sets of duplicative sequence reads in at least one master sequence read file.

8. The method according to claim 7, wherein the at least one master sequence read file is a text file.

9. The method according to claim 7, further comprising collecting meta information for each of the plurality of sequence reads and matching the meta information to a single read in the at least one master sequence read file.

10. The method according to claim 9, wherein the meta information comprises a sequence read ID.

11. The method according to claim 9, wherein the obtaining, identifying, and storing steps are performed by a computer system comprising a processor coupled to a non-transitory memory, and further wherein the collected and matched meta information is stored in a computer-readable output file.

12. The method of claim 11, wherein the sequence reads are stored in the at least one master sequence read file using IUPAC nucleotide characters.

13. The method of claim 12, wherein the at least one master sequence read file and the output file are stored as plain text files, and further wherein the computer system comprises a text editor program capable of opening the plain text files.

14. The method of claim 13, wherein the text editor program is capable of displaying the plain text files on a computer screen showing the meta information and the sequence reads in a human-readable format.

15. The method of claim 7, wherein sequence reads are stored in the at least one master sequence read file using IUPAC nucleotide characters.

* * * * *